United States Patent [19]

Joslin et al.

[11] 4,296,759
[45] Oct. 27, 1981

[54] BLOOD COLLECTION DEVICE AND METHOD WITH ANTI-BACKFLOW MEANS

[75] Inventors: Joel A. Joslin, Sunset Hills; Alan B. Ranford, Des Peres, both of Mo.

[73] Assignee: Sherwood Medical Industries Inc., St. Louis, Mo.

[21] Appl. No.: 810,257

[22] Filed: Jun. 27, 1977

[51] Int. Cl.³ .............................................. A61M 5/00
[52] U.S. Cl. ............................... 128/766; 128/218 NV
[58] Field of Search ............... 128/2 F, 218 NV, 276, 128/DIG. 5, 766, 763

[56] References Cited

U.S. PATENT DOCUMENTS

| 2,518,165 | 8/1950 | Millard | 128/2 F |
|---|---|---|---|
| 3,089,490 | 5/1963 | Goldberg | 128/218 D |
| 3,091,240 | 5/1963 | McConnaughey et al. | 128/218 NV |
| 3,162,195 | 12/1964 | Dick | 128/276 |
| 3,181,529 | 5/1965 | Wilburn | 128/2 F |
| 3,577,980 | 5/1971 | Cohen | 128/2 F |
| 3,659,587 | 5/1972 | Baldwin | 128/2 F |
| 3,734,080 | 5/1973 | Petterson et al. | 128/2 F |
| 3,747,812 | 7/1973 | Karman et al. | 128/215 X |
| 3,874,367 | 4/1975 | Ayres | 128/2 F |
| 4,112,924 | 9/1978 | Ferrara et al. | 128/2 F |

FOREIGN PATENT DOCUMENTS 2349996  2/1974  Fed. Rep. of Germany ... 128/DIG. 5

OTHER PUBLICATIONS

Evacuated Blood-Collection Tubes-The Backflow Hazard, CMA Journal, Aug. 9 1975, vol. 113, pp. 203, 211, 212.

Primary Examiner—John D. Yasko
Attorney, Agent, or Firm—Stanley N. Garber; William R. O'Meara

[57] ABSTRACT

A blood collection tube is provided with a stopper adapted to be pierced by a needle cannula for introducing a sample of blood into the collection tube, and a valve disposed within the tube which allows blood to flow from the proximal end of the needle into the blood collection chamber of the tube but prevents the reflux of blood from the collection chamber to the patient.

4 Claims, 5 Drawing Figures

BLOOD COLLECTION DEVICE AND METHOD WITH ANTI-BACKFLOW MEANS

BACKGROUND OF THE INVENTION

This invention relates to fluid sampling devices and more particularly to blood collection containers for drawing blood samples.

Evacuated containers or tubes having needle pierceable stoppers are used extensively in drawing blood samples for the purpose of conducting laboratory tests on the patient's blood. A conventional method of obtaining a sample is to employ a blood collection tube and a tube and needle holder having a double-ended needle cannula. After the distal end of the cannula is placed in the vein of the patient, the air evacuated blood collection tube is moved in the holder with the tube stopper being guided onto the proximal end of the cannula. The cannula pierces the stopper and the negative pressure in the container facilitates the drawing of blood from the vein of the patient.

In many cases, a number of evacuated containers are filled with blood samples while using the same tube holder and while the cannula remains in the vein of the patient. For example, containers provided with different chemicals may be used to draw a number of blood samples for the purpose of conducting different clinical tests on the patient's blood. Care must be taken to avoid the flowback of drawn blood to the patient since these chemicals may be harmful to the patient. Also, non-sterile tubes are usually used.

When employing conventional tube and needle holders and evacuated collection tubes, faulty techniques in drawing blood can cause withdrawn blood to be returned to the patient. For example, if the contents of the tube is allowed to contact the proximal end of the needle and an employed tourniquet is not removed soon after blood begins to flow or if the arm of the patient is raised, a drop in venous pressure may cause the flowback of blood from the tube to the patient. Also, if a force is applied to the tube in a manner to compress the stopper against the holder while the tube contains blood, a pumping effect may be produced causing withdrawn blood to flow back into the patient.

Valves have been provided in the needle assembly of sampling devices to prevent the backflow of drawn blood from the container or tube to the patient. U.S. Pat. No. 3,874,367, for example, shows a valve disposed in a chamber constructed in a needle assembly between distal and proximal needles for preventing withdrawn blood from returning to the patient. This construction, however, is relatively expensive not only because of the new tooling required in the manufacture of such needle assemblies but because of the additional parts required. Such devices require two needles, two hubs, and the steps of securing each needle to its hub. Such parts and steps result in relatively high manufacturing costs.

SUMMARY OF THE INVENTION

Accordingly, it is an object of the present invention to provide a fluid collection device which prevents backflow of fluid from the collection chamber of the device to the source of the fluid and which is relatively economical. A more specific object of the present invention is to provide a blood collection device which prevents backflow of blood from the collection chamber of the device to the patient, is relatively economical, and wherein it can be employed with conventional needle assemblies and tube holders.

In accordance with one form of the present invention, a collection device is provided that includes an evacuated container closed at one end and having a needle-pierceable stopper closing the opposite end, and a fluid flow one-way valve disposed within the container which allows fluid to flow from the needle to the collection chamber but prevents fluid flow from the collection chamber to the needle.

DESCRIPTION OF THE PREFERRED EMBODIMENTS

Figure 1:
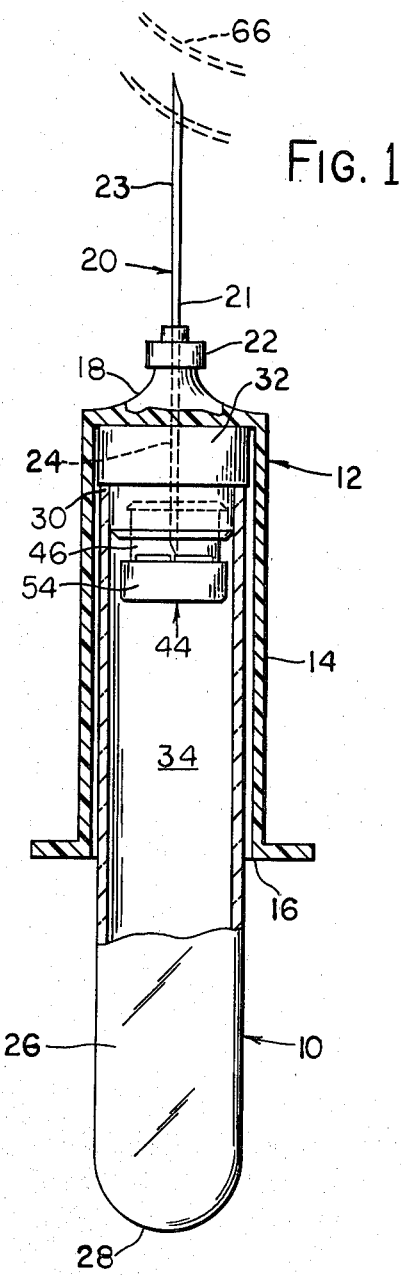
FIG. 1 is a side elevation partly in section of a fluid collection device in accordance with a preferred embodiment of the prevent invention with the device shown disposed in a tube and needle holder.

Referring now to the drawings, and particularly to FIG. 1, a fluid collection device 10 is shown disposed in a conventional tube and needle holder 12. The holder 12 includes a cylindrical barrel 14 having an open lower end 16 for receiving the collection device 10 and an upper closed end 18 carrying a needle assembly 20 having a double-ended needle cannula or hypodermic needle 21. Needle 21 is fixed to a threaded hub 22 that is threadedly connected to the holder 12. The needle 21 extends longitudinally along the axis of the holder and has a distal portion 23 exterior to the holder and a proximal portion 24 extending proximally within the barrel 14.

Figure 2:
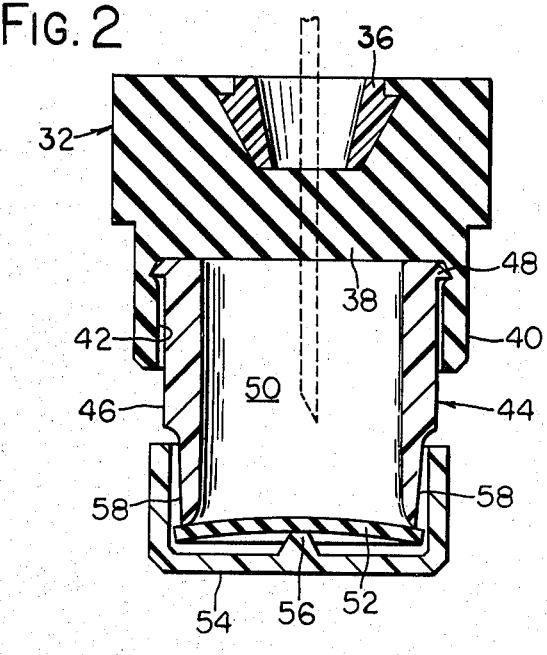
FIG. 2 is an enlarged elevational cross-sectional view of the stopper and fluid pressure responsive valve of FIG. 1.

Collection device 10 includes a blood collection container or tube 26 having an integrally closed bottom end 28 and an upper open end 30 in which is disposed a needle-pierceable stopper 32. The tube 26 is preferably of glass and the stopper 32 is of a suitable elastomeric or rubber material that will maintain a negative pressure within the tube 26. Tube 26 provides a blood collection chamber 34 within the tube below the stopper 32. Stopper 32 is self-sealing after the needle 21 has pierced the stopper and is subsequently removed. In FIG. 2, the stopper 32 is shown provided with a relatively hard needle guide insert 36 which serves to guide the needle into the central portion 38 of the stopper even if it is somewhat off center. The stopper 32 has a lower cylindrical portion 40 which extends into the tube 26 and which is provided with a bottom, central cylindrical recess 42 which is directly below central portion 38.

Disposed within the collection tube 26 below the stopper 32 is a one-way fluid flow valve indicated generally at 44. Valve 44 is received in the recess 42 of the stopper. The valve 44 includes an upper cylindrical body member 46 having an annular ridge 48 which extends outwardly and downwardly from the upper end of the body member and has an outer annular sharp edge which frictionally holds the valve to the underside of stopper 32 within recess 42. The body member 46 has a valve chamber 50 extending through it which is in the series flow path between the needle 21 and collection chamber 34.

Valve 44 has a movable member 52 shown in the form of a resilient rubber diaphragm closing the lower end of the valve chamber 50. Diaphragm 52 is normally held in the valve closed position as shown in FIG. 2, by a lower end cap 54 which is frictionally connected to the lower end portion of the body member 46. Cap 54 is circular and has an upwardly extending central abutment 56 engaging the central portion of the diaphragm to cause the upper marginal surface of the diaphragm 52 to resiliently engage the bottom open end of the body member 46 and sealingly close the bottom end of valve chamber 50. Diaphragm 52 is disc-shaped and preferably formed of a suitable elastomeric or rubber material. The cap 54 is cup-shaped and may be formed of a suitable plastic. Also, the body member 46 can be formed of a suitable plastic material or of metal if desired.

Figure 3:
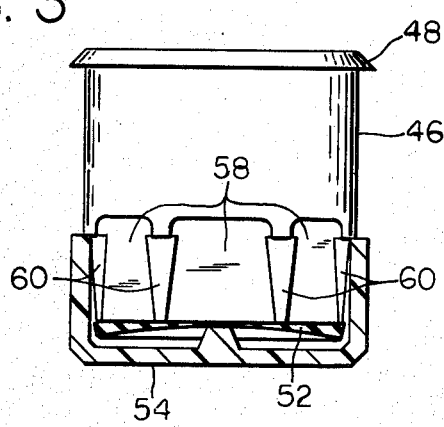
FIG. 3 is a side elevational view partly in section of the valve of FIG. 2, rotated 30°.
Figure 4:
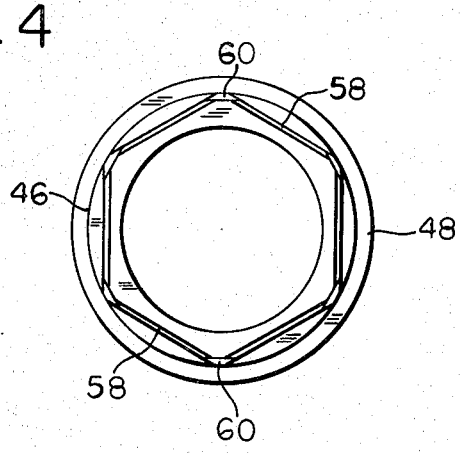
FIG. 4 is a bottom end view of the upper member of the valve of FIG. 2.

As also seen in FIGS. 3 and 4, the upper body member 46 is provided with a plurality of circumferentially spaced flat portions 58 with a plurality of circumferentially spaced arcuate relatively small portions 60 alternating with the flat portions 58. The cap 54 has an inner diameter such that when the lower portion of the body member 46 is inserted into the cap as shown in FIG. 3, the inner walls of the cap frictionally engage the arcuate portions 60 to frictionally hold the cap on the lower end of body 46. The flat portions 58 are spaced from the cap 54 to permit blood to flow between them to collection chamber 34 when the valve is open during the filling of the collection tube.

The stopper 32 and valve 44 may be inserted into the tube 26 while in an air evacuated chamber during assembly of the device 10. The valve chamber 50 and collection chamber 34 are provided with a negative pressure in accordance with the desired amount of blood to be drawn into the collection chamber. With the pressures on opposite sides of the diaphragm 52 equal, the abutment 56 of cap 54 normally maintains the diaphragm 52 in the closed condition as seen in FIG. 2. When a fluid pressure differential exists across the diaphragm 52 such that the pressure in valve chamber 50 is positive with respect to the pressure in collection chamber 34, the peripheral or marginal portions of the diaphragm are moved away from the bottom end of valve member 46 to allow fluid to pass from the valve chamber 50 into cap 54 and then into collection chamber 34.

In use, after the needle assembly 20 is attached to the barrel 14, the distal end 23 of the needle may be inserted into a vein 66 of a patient from whom a blood sample is to be collected. The collection device 10 is then inserted into and guided by the holder 12 toward the proximal end portion 24 of needle 21. When needle portion 24 has fully penetrated the stopper, it enters the valve chamber 50 and fluid communication between the blood in vein 66 and the air evacuated collection chamber 34 is effected. Since the fluid pressure in valve chamber 50 is now positive with respect to the pressure in collection chamber 34, the valve 44 will be opened and blood flows from valve chamber 50 past the diaphragm 52, upwardly into the spaces between the flat portions 58 of the body 46 and the inner walls of the cap 54, downwardly between the inner walls of the tube 26 and the outer walls of the cap, and then into the collection chamber 34. As the collection chamber fills, the pressure differential across the diaphragm 52 will decrease until the pressure is small or substantially equalized, and then the resiliency of the diaphragm will again close against the bottom end of body 46 to close the valve. When valve 44 is closed, no blood can flow from the collection chamber 34 back through the valve and into the patient. Thus, where chemicals or other materials are disposed in the tube 26 by the manufacturer, the blood mixing with such chemicals cannot be inadvertently returned to the patient since the valve 44 is closed to such flow.

Figure 5:
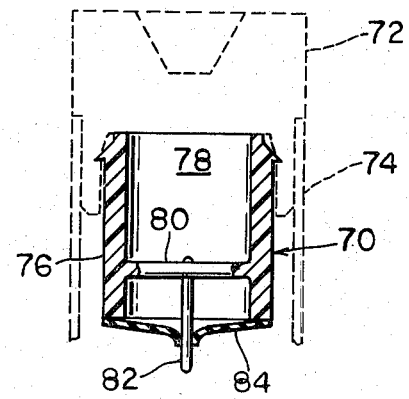
FIG. 5 is a cross-sectional elevational view of a valve in accordance with a modified embodiment.

FIG. 5 shows a one-way valve 70 of modified construction connected to a needle-pierceable rubber stopper shown in phantom at 72 and which is disposed in a blood collection tube which is partially shown in phantom at 74. Valve 70 includes a cylindrical body 76 having a valve chamber 78 and an integral, diametrically extending rod 80. The rod 80 has an axial stem 82 fixed to it which extends axially below the bottom end of body 76. A generally circular or disc-like diaphragm 84 is disposed on the extending lower end of the stem 82. The diaphragm 84 has a central hole of smaller diameter than that of the stem so that the diaphragm can be readily pushed onto the stem to the desired position shown in FIG. 5. The diaphragm 84 is shown resiliently urged against the lower end of the body member to close the bottom of chamber 78. Diaphragm 84 may be formed of any suitable, resilient rubber or other elastomeric material.

Valve 70 of FIG. 5 operates in a manner similar to that of valve 44 of FIG. 1. When a blood collection needle pierces the stopper 72, blood from the patient's vein flows into valve chamber 78 and through the valve to the collection portion of the tube below the stopper and valve. The valve is open to pass this flow of blood since the upper side of the diaphragm will be positive with respect to the negative pressure on the bottom side of the valve.

As a collection tube 74 fills, the original relatively high negative pressure decreases with the pressure differential across the diaphragm 84 also decreasing. When the pressure differential across the valve is relatively low or approaching or reaching zero, the resiliency of the diaphragm causes the marginal surfaces of the upper side of the diaphragm to again sealingly engage the annular bottom end of the body 76 to thereby close the valve 70. Under these conditions, blood in the collection chamber of tube 74 cannot flow past the diaphragm 84 so that this blood cannot be returned to the patient.

In some cases, after the filled collection tube is removed from the holder 12, it is inserted in a centrifuge to separate the serum from the cellular phase for performing laboratory tests on the separated serum. Where serum tests are run in this manner, the embodiment shown in FIGS. 1-4 has the advantage of tending to trap a blood clot in the one-way valve. For example, a blood clot which forms during centrifugation in the blood that may remain in the valve chamber 50, would tend to be wedged and trapped in the spaces between the facing inner walls of the cap 54 and the inclined surfaces 58 of the body member 46. Such a clot would be removed from the tube 26 with the stopper 32 as it is removed to open the tube for extracting the separated serum.

Both of the pressure responsive valves 44 and 70 are disposed in series in the blood flow path from the patient to the container and are responsive to predetermined pressure differentials across their movable valve members, such as the diaphragms, for allowing blood flow in one direction through them, that is, from the valve chamber to the collection chambers. The valves are open only when fluid flows from the valve chamber to the collection chamber. In the closed condition of the two valves, the condition shown in the drawing, the valve chambers 50 and 78 provide closed, fluid or airtight, chambers since one end of each chamber is sealingly closed by the stopper and the opposite end by the movable valve member or diaphragm. With the valve chamber closed in this manner, blood from the valve chamber cannot be returned to the patient since air or blood from the collection chamber could not enter the valve chamber to replace such blood flow. Thus, blood cannot flow back from the collection or valve chamber so that economical non-sterile blood collection devices can be employed.

The stopper and valve are readily assembled together by simply inserting the valve into the stopper recess. This provides a stopper and valve assembly which is readily inserted into the collection tube.

The size or length of the upper valve member or chamber and size of the proximal portion of the needle cannula are so related that when the collection tube is inserted fully into the holder, the lower tip of the needle cannula is within the valve chamber between the stopper and diaphragm.

As various changes could be made in the above construction without departing from the scope of the invention, it is intended that all matter contained in the above description or shown in the accompanying drawing shall be interpreted as illustrative and not in a limiting sense.

What is claimed is:

1. A blood collection device comprising a container having one end closed and a blood collection chamber for receiving a blood sample, a needle-pierceable stopper closing the opposite end of said container and adapted to be pierced by a needle connected to a source of blood, said collection chamber normally having a negative pressure therein, and a fluid pressure differential responsive one-way valve disposed in said container between said stopper and said collection chamber in the path of blood flow from a needle piercing said stopper to said collection chamber and including a pair of valve members relatively movable for opening and closing said valve, said valve being responsive to fluid pressure differentials thereacross such that said valve is open to allow blood flow from the needle through said valve to said collection chamber when the fluid pressure on the needle side of said valve is greater than that on the collection chamber side thereof but is closed to prevent the flow of blood from said collection chamber through said valve to the needle, said valve members being normally sealingly engaged with each other to close said valve, one of said valve members being movable relative to the other said valve members to open said valve and allow blood flow from the needle to said collection chamber when in use, said other valve member being a hollow member providing a valve chamber disposed to receive the tip of a needle piercing said stopper when in use and allowing the passage of blood therethrough to said collection chamber, said one valve member normally closing said valve chamber from said collection chamber, said valve including a generally cup-shaped member connected to said hollow member and normally urging said one valve member into sealing engagement with the botton of said hollow member to close said valve.

2. The device of claim 1 wherein radially inner wall portions of said cup-shaped member and facing radially outer surface portions of said hollow member are spaced to provide blood flow paths from said valve chamber to said collection chamber.

3. The device of claim 2 wherein said blood flow paths narrow at the open end of said cup-shaped member.

4. A blood collection device comprising a container having one end closed and a blood collection chamber for receiving a blood sample, a needle-pierceable stopper closing the opposite end of said container and adapted to be pierced by a needle connected to a source of blood, said collection chamber normally having a negative pressure therein, and a fluid pressure differential responsive one-way valve disposed in said container between said stopper and said collection chamber in the path of blood flow from a needle piercing said stopper to said collection chamber and including a pair of valve members relatively movable for opening and closing said valve, said valve being responsive to fluid pressure differentials thereacross such that said valve is open to allow blood flow from the needle through said valve to said collection chamber when the fluid pressure on the needle side of said valve is greater than that on the collection chamber side thereof but is closed to prevent the flow of blood from said collection chamber through said valve to the needle, said stopper extending into said opposite end of said container in sealing engagement with the internal side walls of said container, said stopper having a recess, said valve having a body received in said recess and frictionally engaging the side walls of said recess, said body having a valve chamber open at the upper end, one of said relatively movable valve members being spaced from said upper end and normally closing said valve chamber, said one valve member being responsive to a predetermined fluid pressure differential between the pressures on opposite sides of said one valve member to open said valve chamber to said collection chamber only for blood flow from said valve chamber to said collection chamber, said body having an axially extending pin within said container, and said one valve member having a central opening with side walls frictionally receiving said pin to normally hold said one valve member in sealing engagement with said body to close said valve chamber from said collection chamber.

* * * * *